(12) United States Patent
Rao et al.

(10) Patent No.: US 7,888,539 B2
(45) Date of Patent: Feb. 15, 2011

(54) AZEOTROPE COMPOSITIONS OF OCTAFLUOROCYCLOBUTANE AND USES THEREOF

(75) Inventors: Velliyur Nott Mallikarjuna Rao, Wilmington, DE (US); Jeffrey P. Knapp, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 417 days.

(21) Appl. No.: 12/033,199

(22) Filed: Feb. 19, 2008

(65) Prior Publication Data

US 2009/0005618 A1    Jan. 1, 2009

Related U.S. Application Data

(60) Provisional application No. 60/903,220, filed on Feb. 23, 2007.

(51) Int. Cl.
*C07C 17/38* (2006.01)
*C09K 11/08* (2006.01)
(52) U.S. Cl. .................. 570/178; 252/301.4 H
(58) Field of Classification Search ................. 570/178; 252/301.4 H
See application file for complete search history.

(56) References Cited

U.S. PATENT DOCUMENTS

| 5,918,481 | A | * | 7/1999 | Pham et al. .................. 62/631 |
| 6,184,426 | B1 | | 2/2001 | Belen'Kill et al. |
| 2005/0230657 | A1 | * | 10/2005 | Leck et al. .................. 252/67 |
| 2008/0051612 | A1 | | 2/2008 | Knapp et al. |

FOREIGN PATENT DOCUMENTS

| EP | 0455399 A2 * | 4/1991 |
| JP | HEI-5-179043 | 7/1993 |

OTHER PUBLICATIONS

Szapiro, variation of azeotropic composition with pressure, Chemical abstract DN: 52:109931, 1958.*
Schotte, "Collection of Phase Equilibrium Data for Separation Technology", Ind. Eng. Chem. Process Des. Dev., 19, 1980, pp. 432-439.
"Phase Equilibrium in Process Design", Wiley-Interscience Publisher, 1970.
Walas, "Activity Coefficients", Phase Equilibria in Chemical Engineering, published by Butterworth Publishers, 1985, pp. 165-244.

* cited by examiner

*Primary Examiner*—Jafar Parsa

(57) ABSTRACT

The present disclosure related to azeotrope and near-azeotrope compositions comprising PFC-C318 and HFC-236cb. The present disclosure further relates to processes for removing PFC-C318 from HFC-236cb. And the present disclosure further relates to azeotrope and near azeotrope compositions comprising hydrogen fluoride and PFC-C318.

10 Claims, 3 Drawing Sheets

US 7,888,539 B2

AZEOTROPE COMPOSITIONS OF OCTAFLUOROCYCLOBUTANE AND USES THEREOF

CROSS REFERENCE TO RELATED APPLICATIONS

This application claims the priority benefit of U.S. Provisional Application 60/903,220, filed Feb. 23, 2008.

BACKGROUND OF THE INVENTION

1. Field of the Invention

The present disclosure relates to azeotrope and azeotrope-like compositions of fluorocarbon compounds. In particular, the present disclosure relates to an azeotrope composition comprising octafluorocyclobutane and 1,1,1,2,2,3-hexafluoropropane and an azeotrope composition comprising octafluorocyclobutane and hydrogen fluoride that are useful in processes to manufacture and purify fluorocarbons.

2. Description of Related Art

Halogenated compounds, especially fluorinated compounds, such as fluorocarbons and hydrofluorocarbons, have been widely used in the industry as for instance, refrigerants, solvents, cleaning agents, foam expansion agents, aerosol propellants, heat transfer media (e.g., heat transfer fluids, and refrigerants), dielectrics, fire extinguishing agents, sterilants and power cycle working fluids.

Processes for the production of 1,1,1,2,2,3-hexafluoropropane (HFC-236cb) by reaction of tetrafluoroethylene monomer ($CF_2=CF_2$ or TFE) with difluoromethane ($CH_2F_2$ or HFC-32) in the presence of antimony pentafluoride ($SbF_5$) catalyst have been described in U.S. Pat. No. 6,184,426.

Current commercially produced TFE is a monomer in the manufacture of a variety of fluorinated polymers, such as polytetrafluoroethylene (PTFE), among others. The various processes used for the manufacture of TFE monomer frequently produce a variety of co-products that are unacceptable in a polymer feedstock, and these TFE monomer manufacturing processes incur significant expense both in equipment and operating costs to remove any such co-products down to low levels to produce high-purity TFE. These purification steps typically increase the production costs for TFE by as much as 20%. Such co-products are considered unacceptable in the TFE starting material because of their adverse effect on the properties of the polymer materials produced from the TFE.

Octafluorocyclobutane (cyclo-$C_4F_8$, or PFC-C318) is one such co-product that may be produced in the manufacture of TFE. TFE used in a reaction with HFC-32 to produce HFC-236cb need not be purified to the same degree as that used as monomer, and may therefore contain some amount of PFC-C318. HFC-236cb may be used as a starting material for the production of certain fluoroolefins, which have been suggested as low global warming alternatives to existing working fluids such as those mentioned previously. If PFC-C318 is present in the TFE feedstock to produce HFC-236cb, it is expected to remain unreacted through the process and be removed with the HFC-236cb product.

It has been surprisingly discovered that PFC-C318 and HFC-236cb form an azeotrope composition. This azeotrope may be useful in various separation schemes to ultimately allow the production of HFC-236cb with appropriate purity to be used in processes for the manufacture of other fluorocarbons including fluoroolefins.

SUMMARY OF THE INVENTION

The present disclosure relates to an azeotrope or near-azeotrope composition comprising PFC-C318 and HFC-236cb.

The present disclosure further relates to a process for the removal of PFC-C318 from a mixture comprising HFC-236cb and PFC-C318, said process comprising: a) subjecting said mixture comprising HFC-236cb and PFC-C318 to a distillation step; and b) removing as distillate a composition comprising an azeotrope or near-azeotrope composition comprising HFC-236cb and PFC-C318.

The present disclosure further relates to a process for the separation of PFC-C318 from a mixture comprising HFC-236cb and PFC-C318, said process comprising: a) subjecting said mixture to a first distillation step in which a composition enriched in either (i) PFC-C318 or (ii) HFC-236cb is removed as a first distillate composition with a first bottoms composition being enriched in the other of said components (i) or (ii); and b) subjecting said first distillate composition to a second distillation step conducted at a different pressure than the first distillation step in which the component enriched as first bottoms composition in (a) is removed in a second distillate composition with a second bottoms composition enriched in the same component which was enriched in the first distillate composition.

The present disclosure further relates to an azeotrope or near-azeotrope composition comprising hydrogen fluoride and PFC-C318.

BRIEF DESCRIPTION OF THE DRAWING(S)

DETAILED DESCRIPTION OF THE INVENTION

Figure 1:
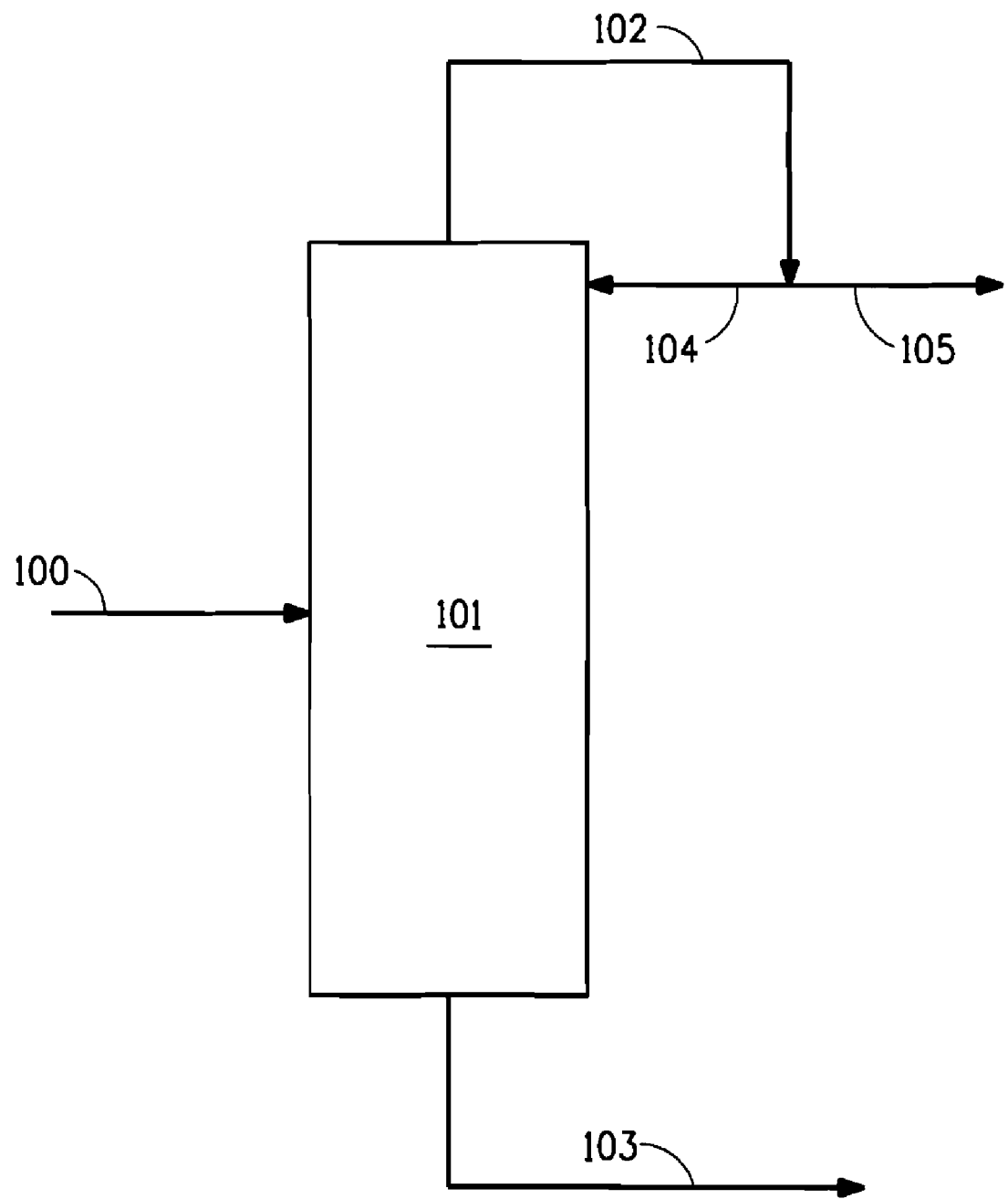
FIG. 1 is a schematic flow diagram illustrating one embodiment for practicing a process for removing PFC-C318 from a composition comprising HFC-236cb and PFC-C318, wherein said process comprises one distillation step.

In one embodiment, the present disclosure provides a composition comprising octafluorocyclobutane (PFC-C318) and 1,1,1,2,2,3-hexafluoropropane ($CF_3CF_2CH_2F$, HFC-236cb). PFC-C318 is a commercially available product (from E.I. du Pont de Nemours & Co., Wilmington, Del.). HFC-236cb may be prepared by reaction of tetrafluoroethylene monomer ($CF_2=CF_2$ or TFE) and difluoromethane ($CH_2F_2$ or HFC-32) as starting materials and using antimony pentafluoride ($SbF_5$) as a catalyst, as described in U.S. Pat. No. 6,184,426.

In another embodiment, the present disclosure provides an azeotrope or near-azeotrope composition comprising effective amounts of PFC-C318 and HFC-236cb.

In another embodiment, the present disclosure provides an azeotrope or near-azeotrope composition comprising effective amounts of PFC-C318 and HFC-236cb.

One aspect provides a composition, which comprises PFC-C318 and an effective amount of HFC-236cb to form an azeotrope or near-azeotrope composition. By effective amount is meant an amount, which, when combined with PFC-C318, results in the formation of an azeotrope or near-azeotrope mixture. As recognized in the art, an azeotrope or a near-azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling.

As used herein, an azeotrope composition is a constant boiling liquid admixture of two or more substances wherein the admixture distills without substantial composition change and behaves as a constant boiling composition. Constant boiling compositions, which are characterized as azeotropic, exhibit either a maximum or a minimum boiling point, as compared with that of the non-azeotropic mixtures of the same substances. Azeotropic compositions as used herein include homogeneous azeotropes which are liquid admixtures of two or more substances that behave as a single substance, in that the vapor, produced by partial evaporation or distillation of the liquid, has the same composition as the liquid. Azeotropic compositions as used herein also include heterogeneous azeotropes where the liquid phase splits into two or more liquid phases. In these embodiments, at the azeotrope point, the vapor phase is in equilibrium with two liquid phases and all three phases have different compositions. If the two equilibrium liquid phases of a heterogeneous azeotrope are combined and the composition of the overall liquid phase calculated, this would be identical to the composition of the vapor phase.

For the purpose of this discussion, near-azeotrope composition (also sometimes referred to as an "azeotrope-like composition") means a composition that behaves in a similar manner to an azeotrope (i.e., has substantially constant boiling characteristics or a tendency not to fractionate substantially upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-azeotrope compositions in which during boiling or evaporation, the liquid composition changes to a substantial degree.

Additionally, near-azeotrope compositions exhibit dew point pressure and bubble point pressure with virtually no pressure differential. That is to say that the difference in the dew point pressure and bubble point pressure at a given temperature will be a small value. It may be stated that compositions with a difference in dew point pressure and bubble point pressure of less than or equal to 3 percent (based upon the bubble point pressure) may be considered to be a near-azeotrope.

Accordingly, the essential features of an azeotrope or a near-azeotrope composition are that at a given pressure, the boiling point of the liquid composition is fixed and that the composition of the vapor above the boiling composition is essentially that of the boiling liquid composition (i.e., little or no fractionation of the components of the liquid composition takes place). It is also recognized in the art that both the boiling point and the weight percentages of each component of the azeotrope composition may change when the azeotrope or near-azeotrope liquid composition is subjected to boiling at different pressures. Thus, an azeotrope or a near-azeotrope composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotrope compositions (including their boiling points at particular pressures) may be calculated (see, e.g., W. Schotte Ind. Eng. Chem. Process Des. Dev. (1980) 19, 432-439). Experimental identification of azeotrope compositions involving the same components may be used to confirm the accuracy of such calculations and/or to modify the calculations at the same or other temperatures and pressures.

Compositions may be formed that comprise azeotrope or near-azeotrope combinations of HFC-236cb with PFC-C318. These include compositions comprising from about 28.7 mole percent to about 37.7 mole percent HFC-236cb and from about 71.3 mole percent to about 62.3 mole percent PFC-C318 (which forms an azeotrope boiling at a temperature from between about −50° C. and about 110° C. and at a pressure from between about 1.68 psi (11.6 kPa) and about 378 psi (2606 kPa)). Preferably, the compositions include from about 31 mole percent to about 36 mole percent HFC-236cb and from about 69 mole percent to about 64 more percent PFC-C318. The azeotrope compositions containing HFC-236cb and PFC-C318 are homogeneous azeotropes in that a single liquid composition is in equilibrium with the vapor composition at a given temperature and pressure.

Compositions may be formed that consist essentially of azeotrope or near-azeotrope combinations of HFC-236cb with PFC-C318. These include compositions consisting essentially of from about 28.7 mole percent to about 37.7 mole percent HFC-236cb and from about 71.3 mole percent to about 62.3 mole percent PFC-C318 (which forms an azeotrope boiling at a temperature from between about −50° C. and about 110° C. and at a pressure from between about 1.68 psi (11.6 kPa) and about 378 psi (2606 kPa)). Additional components to the azeotrope or near azeotrope composition would also be present, but would not materially effect or change the azeotropic properties of the composition.

At atmospheric pressure, the boiling points of HFC-236cb and PFC-C318 are about −0.98° C. and −5.98° C., respectively. The relative volatility at 41 psi (288 kPa) and 20.18° C. of HFC-236cb and PFC-C318 was found to be nearly 1.0 as 33.0 mole percent HFC-236cb and 67.0 mole percent PFC-C318 was approached. These data indicate that the use of conventional distillation procedures will not result in the separation of a substantially pure compound because of the low value of relative volatility of the compounds.

To determine the relative volatility of HFC-236cb with PFC-C318, the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126, the entire disclosure of which is hereby incorporated by reference. Samples of the vapor and liquid, or vapor and each of the two liquid phases under those conditions where two liquid phases exist, were obtained and analyzed to verify their respective compositions.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", $4^{th}$ Edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not mixtures of HFC-236cb and PFC-C318 behave in an ideal manner, and can sufficiently predict the relative volatilities of the components in such mixtures. Thus, while HFC-236cb has a good relative volatility compared to PFC-C318 at low PFC-C318 concentrations, the relative volatility becomes nearly 1.0 as 67.0 mole percent PFC-C318 was approached at 20.18° C. This would make it impossible to separate PFC-C318 from HFC-236cb by conventional distillation from such a mixture. Where the relative volatility approaches 1.0 defines the system as forming a near-azeotrope or azeotrope composition.

It has been found that azeotropes of PFC-C318 and HFC-236cb are formed at a variety of temperatures and pressures. Azeotrope compositions may be formed between 11.6 kPa (at a temperature of −50° C.) and 2606 kPa (at a temperature of 110° C.) said compositions consisting essentially of from about 62.3 mole percent to about 71.3 mole percent PFC-C318 and from about 37.7 mole percent to about 28.7 mole percent HFC-236cb. An azeotrope of HFC-236cb and PFC-C318 has been found at 20.18° C. and 41.8 psi (288 kPa) consisting essentially of about 33.0 mole percent HFC-236cb and about 67.0 mole percent PFC-C318. Based upon the above findings, azeotrope compositions at other temperatures and pressures may be calculated. It has been calculated that an azeotrope composition of about 28.7 mole percent HFC-236cb and about 71.3 mole percent PFC-C318 can be formed at −50° C. and 1.68 psi (11.6 kPa) and an azeotrope composition of about 35.5 mole percent HFC-236cb and about 62.3 mole percent PFC-C318 can be formed at 110° C. and 378 psi (2606 kPa). Accordingly, one aspect provides an azeotrope or near-azeotrope composition consisting essentially of from about 28.7 mole percent to about 37.7 mole percent HFC-236cb and from about 71.3 mole percent to about 62.3 mole percent PFC-C318, said composition having a boiling point of from about −50° C. at 1.68 psi (11.6 kPa) to about 110° C. at 378 psi (2606 kPa).

In another embodiment, the present disclosure provides an azeotrope or near-azeotrope composition comprising hydrogen fluoride (HF) and PFC-C318. More preferably an effective amount of PFC-C318 is used. The azeotrope composition has been measured at three temperatures (−10, 40, and 70° C.).

In another embodiment, the present disclosure provides an azeotrope or near-azeotrope composition comprising from about 39.5 mole percent to about 59.5 mole percent hydrogen fluoride and from about 60.5 mole percent to about 40.5 mole percent PFC-C318, wherein the vapor pressure is from about 1.81 psi (12.5 kPa) to about 565 psi (3896 kPa) at a temperature of from about −50° C. to about 100° C.

In another embodiment, the present disclosure provides an azeotrope or near-azeotrope composition wherein said composition consists essentially of from about 39.5 mole percent to about 59.5 mole percent hydrogen fluoride and from about 60.5 mole percent to about 40.5 mole percent PFC-C318, wherein the vapor pressure is from about 1.81 psi (12.5 kPa) to about 565 psi (3896 kPa) at a temperature of from about −50° C. to about 100° C.

The HFC-236cb/PFC-C318 azeotrope compositions are useful in processes to produce HFC-236cb and in processes to purify HFC-236cb. In fact, the HFC-236cb/PFC-C318 azeotrope and near-azeotrope compositions may be useful in any process that creates a composition containing PFC-C318 and HFC-236cb.

In one embodiment, the PFC-C318 may be present in the HFC-236cb because it is an impurity in the TFE fed to a reactor along with HFC-32 for the production of HFC-236cb. The PFC-C318 concentration in the crude HFC-236cb product stream (after HFC-32 and low boiling component removal from the HFC-236cb product) may be from about 20 molar parts per million (ppm) to about 100 ppm. Removal of the PFC-C318 from HFC-236cb may be accomplished with a single distillation column, whereby the azeotrope or near-azeotrope composition is taken overhead in the distillate. This near-azeotropic distillate, which contains almost all of the PFC-C318 in the column feed, may be collected and purified in any appropriate manner or discarded. The loss of HFC-236cb with the PFC-C318 in the distillate would be minimal. The bottoms stream leaving the column would be essentially free of PFC-C318.

As described herein, by "essentially free of PFC-C318" (or any other component) is meant that the composition contains less than about 100 ppm (mole basis), preferably less than about 10 ppm and most preferably less than about 1 ppm, of PFC-C318 (or of the component mentioned previously above).

In one embodiment the present disclosure provides a process for the removal of PFC-C318 from a mixture comprising HFC-236cb and PFC-C318, said process comprising: a) subjecting said mixture comprising HFC-236cb and PFC-C318 to a distillation step; and b) removing as distillate a composition comprising an azeotrope or near-azeotrope composition comprising HFC-236cb and PFC-C318.

Referring to FIG. 1, in one embodiment the feed composition (100), containing an assumed 99.99 mol % HFC-236cb and 100 ppm PFC-C318, is fed to any point between the top and bottom stage of distillation column 101. In another embodiment, the feed composition is fed to a stage near the mid-point of the column. Distillation column (101) contains 40 theoretical stages and operates with a head pressure of 130 kPa. The distillate stream is split into reflux 104 and output 105 streams. The reflux flow (104) is two times the column feed rate (100). Column (101) is operated such that the purified HFC-236cb stream leaving the bottom of the column (103) contains 1 ppm of PFC-C318. The distillate composition (102) leaving the top of the column contains approximately 99% of the PFC-C318 from the column feed (100), but only a very small amount (0.005%) of the HFC-236cb from the feed. The distillate stream (102) contains 33.62 mol % HFC-236cb, which is close to the azeotropic composition of roughly 32 mol % HFC-236cb at 130 kPa.

In an alternative embodiment, the PFC-C318 may be removed from the HFC-236cb by a 2 column azeotropic distillation (also known as pressure swing distillation).

In one embodiment, the present disclosure provides a process for the separation of PFC-C318 from a mixture comprising HFC-236cb and PFC-C318, said process comprising: a) subjecting said mixture to a first distillation step in which a composition enriched in either (i) PFC-C318 or (ii) HFC-236cb is removed as a first distillate composition with a first bottoms composition being enriched in the other of said components (i) or (ii); and b) subjecting said first distillate composition to a second distillation step conducted at a different pressure than the first distillation step in which the component enriched as first bottoms composition in (a) is removed in a second distillate composition with a second bottoms composition enriched in the same component which was enriched in the first distillate composition.

In one embodiment of the present disclosure, in a process to produce a fluoroolefin comprising 1,2,3,3,3-pentafluoropropene ($CF_3CF=CHF$, or HFC-1225ye), wherein the first step is reaction of TFE and HFC-32 to produce HFC-236cb, there may be seen additional utility for the HFC-236cb/PFC-C318 azeotrope compositions. The second step of the process to produce HFC-1225ye may comprise a dehydrofluorination step wherein a molecule of hydrogen fluoride (HF) is removed from the HFC-236cb thereby forming the HFC-1225ye.

Figure 2:
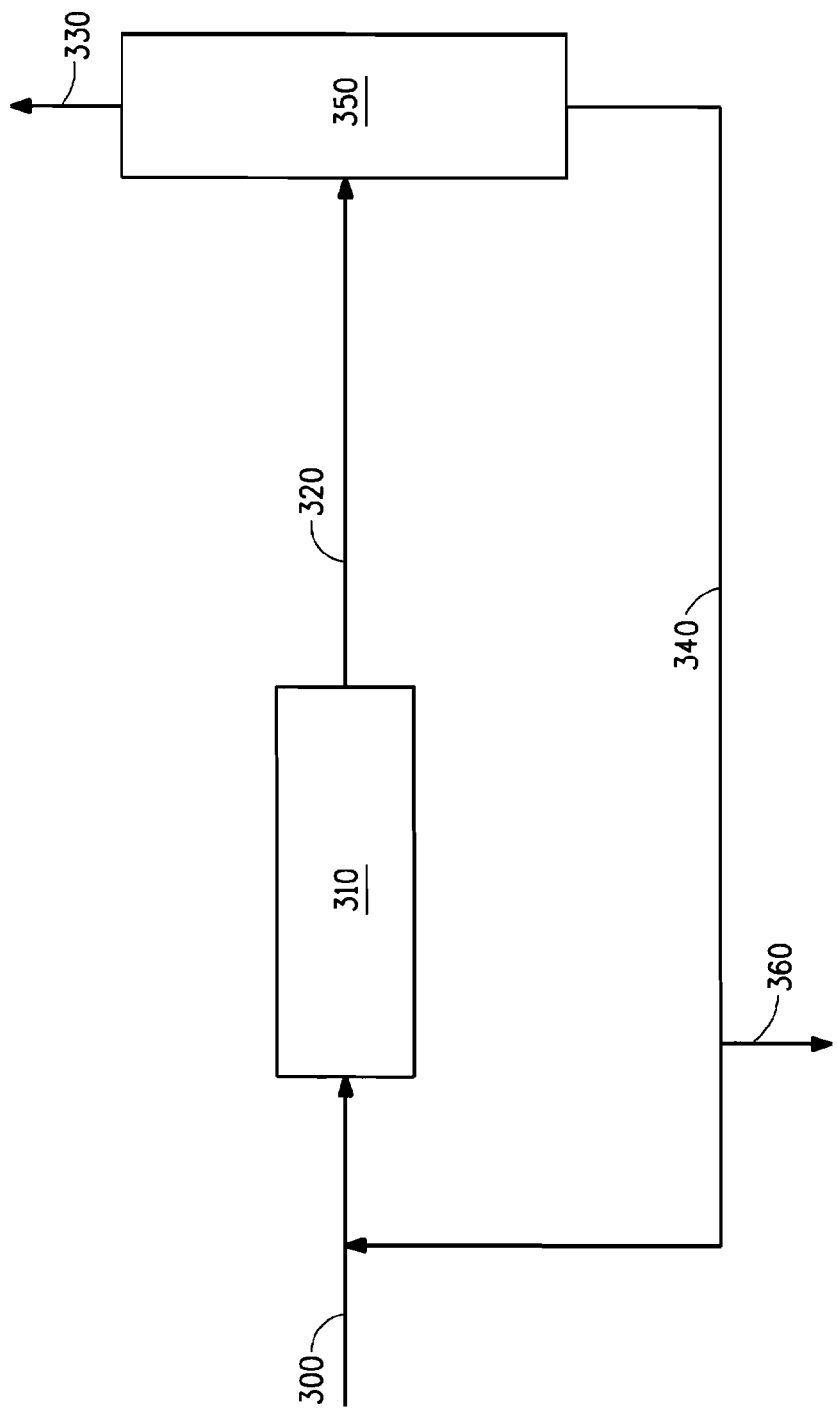
FIG. 2 is a schematic diagram of a dehydrofluorination process.

If the PFC-C318 is not removed from the HFC-236cb product from the TFE/HFC-32 reaction and this predominantly HFC-236cb stream is fed to a dehydrofluorination reactor, a portion of the HFC-236cb may be converted to HFC-1225ye, but the PFC-C318 would pass through the reactor unchanged and flow to the recycle column along with the unreacted HFC-236cb and the product of the reaction being HF, HFC-1225ye, and other potential by-products. A dehydrofluorination process is shown in FIG. 2. Referring to FIG. 2, fresh HFC-236cb is fed via line 300 to a dehydrofluorination reactor 310. The reaction products are fed via line 320 to recycle column 350. The crude HFC-1225ye and hydrogen fluoride are taken overhead from column 350 as a distillate 330. The unreacted HFC-236cb is taken off the bottom of column 350 and can be recycled to the reactor 310 via line 340. Optionally, a purge 360 can be taken off the recycle line 340 before feeding back to the reactor to remove PFC-C318 from the recycle stream overtime. As disclosed in U.S. patent application Ser. No. 11/844,403, filed Aug. 24, 2007, the recycle column using the lower boiling HF/HFC-1225ye azeotrope may be used to distill all of the HF overhead, creating an essentially acid-free bottoms stream, comprising most of the unreacted HFC-236cb, which is recycled to the reactor.

In one embodiment, the recycle column may be operated such that the majority of the PFC-C318 present distills overhead with the HF and HFC-1225ye. In this embodiment, the PFC-C318/HFC236cb separation is accomplished by use of the HF/PFC-C318 azeotrope. Then, in a subsequent separation step, the PFC-C318 may be removed from the HFC-1225ye product.

In another embodiment, the recycle column may be operated such that the majority of the PFC-C318 is removed from the bottom of the column with the unreacted HFC-236cb and recycled to the reactor. In this embodiment, the concentration of PFC-C318 in the reactor recycle stream will increase over time until the PFC-C318 is removed. Removal of PFC-C318 from the recycle stream may be accomplished via a simple purge stream or by some other separation process such as pressure-swing distillation. The separation process would be located where the purge is shown in FIG. 2.

This example demonstrates the use of pressure-swing distillation to remove PFC-C318 from HFC-236cb. Again, the PFC-C318 concentration would be higher for this case than the 100 ppm (molar) used in the first example. A PFC-C318 concentration of 5 mol % is assumed for this example.

Figure 3:
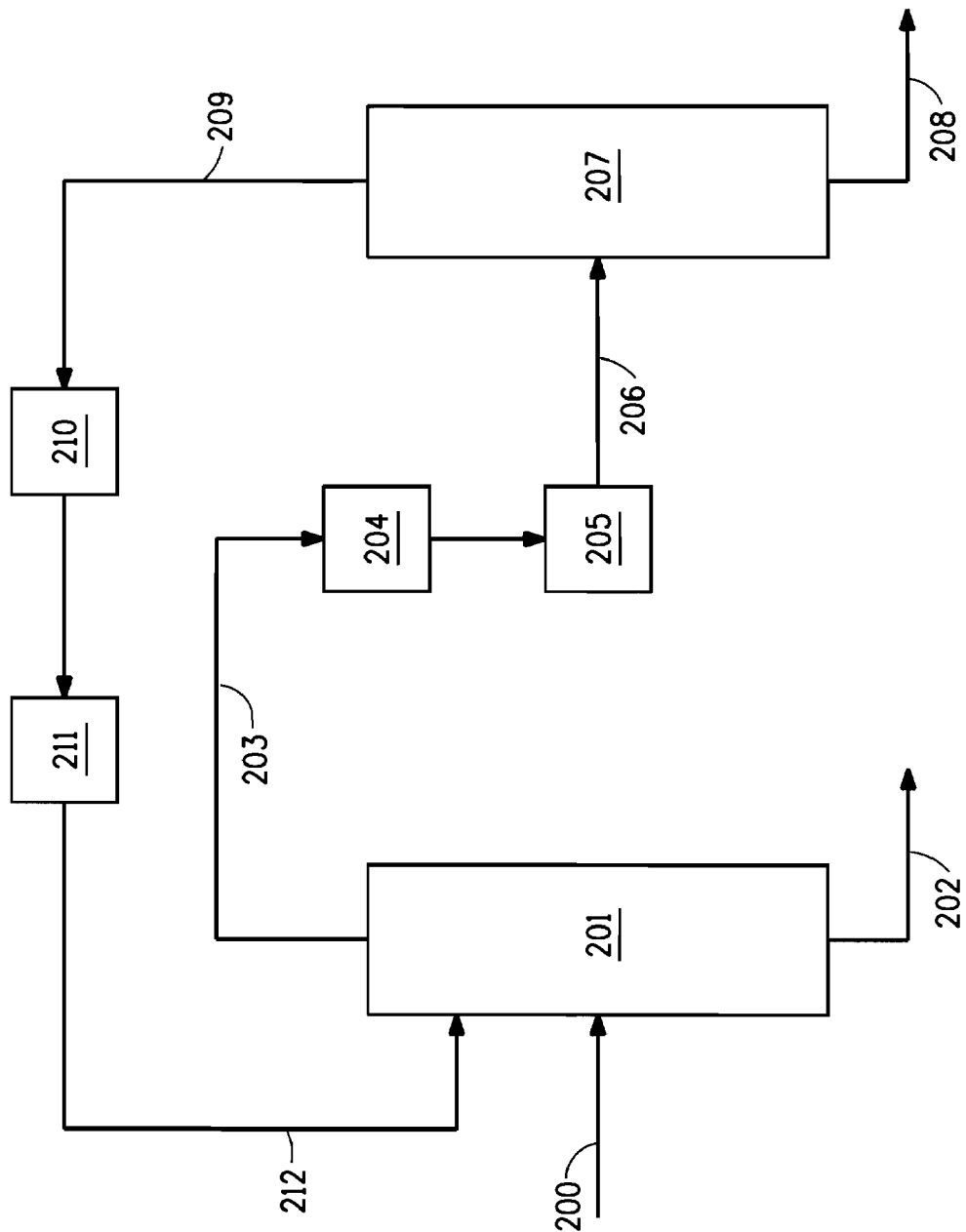
FIG. 3 is a schematic diagram of a process for separating PFC-C318 from a composition comprising HFC-236cb and PFC-C318, wherein said process comprises 2 distillation steps.

Referring to FIG. 3, in one embodiment, a feed stream (200), containing about 99.5 mol % HFC-236cb and about 5 mol % PFC-C318, is fed to a point between the top and bottom stage of distillation column (201). In another embodiment, the feed stream is fed to a stage near the mid-point of the column. Distillation column (201) contains 50 theoretical stages and operates with a head pressure of 120 kPa. Though not explicitly shown in FIG. 3, column (201) includes devices known to those skilled in the art for adding heat to the bottom of the column and removing heat from the top of the column. A reflux flow of four times the column feed (200) flow rate is used. Column (201) is operated such that the purified HFC-236cb stream leaving the bottom of the column (202) contains 10 ppm of PFC-C318 and the majority of the HFC-236cb from stream (200). The distillate stream (203) leaving the top of the column contains 33.82 mol % HFC-236cb, which is on the HFC-236cb-rich side and close to the azeotropic composition at 120 kPa. Stream (203) is then increased in pressure using a device (204), such as a pump, and then optionally heated in (205), using a device such as a heat exchanger, to form stream (206), the feed to a second distillation column (207), which is operated at an elevated pressure. In one embodiment of the process, the pressure in (207) is chosen such that the composition of the feed stream (206) lies on the PFC-C318-rich side of the azeotrope at the column (207) pressure.

In one embodiment, the process may be operated such that the column (201) bottoms composition (stream 202) comprises HFC-236cb essentially free of PFC-C318.

In another embodiment, the process may be operated such that the column (207) bottoms composition (stream 208) comprises PFC-C318 essentially free of HFC-236cb.

EXAMPLES

Example 1

Phase Studies of Mixtures of HFC-236cb and PFC-C318

A phase study was performed for a composition consisting essentially of PFC-C318 and HFC-236cb, wherein the composition was varied and the vapor pressures were measured at 20.18° C. Based upon the data from the phase study, azeotrope compositions at other temperatures and pressures have been calculated.

Table 1 provides a compilation of experimental and calculated azeotrope compositions for HFC-236cb and PFC-C318 at specified temperatures and pressures.

TABLE 1

| Temperature, ° C. | Pressure, psi (kPa) | Mole % PFC-C318 | Mole % HFC-236cb |
|---|---|---|---|
| −50.0 | 1.68 (11.6) | 71.3 | 28.7 |
| −40.0 | 3.07 (21.2) | 70.5 | 29.5 |
| −30.0 | 5.28 (36.4) | 69.8 | 30.2 |
| −20.0 | 8.62 (59.4) | 69.1 | 30.9 |
| −10.0 | 13.5 (93.1) | 68.5 | 31.5 |
| 0.0 | 20.3 (140) | 68.0 | 32.0 |
| 10.0 | 29.5 (203) | 67.5 | 32.5 |
| 20.18 | 41.8 (288) | 67.0 | 33.0 |
| 30.0 | 57.1 (394) | 66.5 | 33.5 |
| 40.0 | 76.7 (529) | 66.1 | 33.9 |
| 50.0 | 101 (696) | 65.6 | 34.4 |
| 60.0 | 130 (896) | 65.2 | 34.8 |
| 70.0 | 166 (1144) | 64.7 | 35.3 |
| 80.0 | 209 (1440) | 64.4 | 35.6 |
| 90.0 | 260 (1790) | 64.1 | 35.9 |
| 100 | 322 (2220) | 64.1 | 35.9 |
| 110 | 378 (2606) | 62.3 | 37.7 |

Example 2

Dew Point and Bubble Point Vapor Pressures for HFC-236cb/PFC-C318

The dew point and bubble point vapor pressures for compositions containing HFC-236cb and PFC-C318 were calculated from measured and calculated thermodynamic properties. The near-azeotrope range is indicated by the minimum and maximum concentration of HFC-236cb (mole percent, mol %) for which the difference in dew point and bubble point pressures is less than or equal to 3% (based upon bubble point pressure). The results are summarized in Table 2.

TABLE 2

| Temperature, | Azeotrope composition, | Near-azeotrope compositions, mol % HFC-236cb | |
|---|---|---|---|
| ° C. | mol % HFC-236cb | Minimum | Maximum |
| −10 | 31.5 | 0.1 | 55.4 |
| 20 | 33.0 | 0.1 | 65.8 |
| 60 | 34.8 | 0.1 | 99.9 |
| 100 | 35.9 | 0.1 | 99.9 |

Example 3

Phase Studies of Mixtures of Hydrogen Fluoride and PFC-C318

A phase study was performed for a composition consisting essentially of PFC-C318 and hydrogen fluoride, wherein the composition was varied and the vapor pressures were measured at −10, 40, and 70° C. Based upon the data from the phase study, azeotrope compositions at other temperatures and pressures have been calculated.

Table 3 provides azeotrope compositions for hydrogen fluoride and PFC-C318 at specified temperatures and pressures.

TABLE 3

| Temperature, ° C. | Pressure, psi | Mole % HF | Mole % PFC-C318 |
|---|---|---|---|
| −50.0 | 1.81 | 59.5 | 40.5 |
| −40.0 | 3.34 | 58.8 | 41.2 |
| −30.0 | 5.80 | 57.7 | 42.3 |
| −20.0 | 9.61 | 56.7 | 43.3 |
| −10.0 | 15.2 | 55.6 | 44.4 |
| 0.0 | 23.3 | 54.7 | 45.3 |
| 10.0 | 34.4 | 53.8 | 46.2 |
| 20.0 | 49.5 | 52.9 | 47.1 |
| 30.0 | 69.4 | 52.2 | 47.8 |
| 40.0 | 95.1 | 51.4 | 48.6 |
| 50.0 | 128 | 50.7 | 49.3 |
| 60.0 | 170 | 50.0 | 50.0 |
| 70.0 | 223 | 49.2 | 50.8 |
| 80.0 | 290 | 48.1 | 51.9 |
| 90.0 | 378 | 46.2 | 53.8 |
| 100 | 565 | 39.5 | 60.5 |

Example 4

Dew Point and Bubble Point Vapor Pressures for PFC-C318/Hydrogen Fluoride

The dew point and bubble point vapor pressures for compositions containing PFC-C318 and hydrogen fluoride were calculated from measured and calculated thermodynamic properties. The near-azeotrope range is indicated by the minimum and maximum concentration of hydrogen fluoride (mole percent, mol %) for which the difference in dew point and bubble point pressures is less than or equal to 3% (based upon bubble point pressure). The results are summarized in Table 4.

TABLE 4

| Temperature, | Azeotrope composition, | Near azeotrope compositions, mol % hydrogen fluoride | |
|---|---|---|---|
| ° C. | mol % hydrogen fluoride | Minimum | Maximum |
| −20 | 56.7 | 33.0 | 62.8 |
| 20 | 52.9 | 35.8 | 58.6 |
| 60 | 50.0 | 37.6 | 56.0 |
| 100 | 39.5 | 35.4 | 48.8 |

Example 5

Azeotropic Distillation of HFC-236cb/PFC-C318 Mixture

A mixture of HFC-236cb and PFC-C318 is fed to a distillation column for the purpose of removing PFC-C318. The data in Table 5 were obtained by calculation using measured and calculated thermodynamic properties. The stream ID numbers at the top of the table refer to FIG. 1.

TABLE 5

| Component or variable | Feed (100) | Distillate (102) | Bottoms (103) | Reflux (104) |
|---|---|---|---|---|
| HFC-236cb (wt %) | 99.99 | 27.8 | 100 | 27.8 |
| PFC-C318 (wt %) | 0.01 | 72.2 | <1 ppm | 72.2 |
| Temperature (° C.) | 5.0 | −2.1 | 5.5 | −2.1 |
| Pressure (kPa) | 200 | 130 | 132 | 130 |

Example 6

Pressure Swing Distillation of HFC-236cb/PFC-C318 Mixture

A mixture of HFC-236cb and PFC-C318 is fed to a distillation process for the purpose of removing (or separating) PFC-C318 from the HFC-236cb (or purification of HFC-236cb). The data in Table 6 were obtained by calculation using measured and calculated thermodynamic properties. The stream ID numbers at the top of the table refer to FIG. 3.

TABLE 6

| Component or variable | Feed (200) | First Column bottoms (202) | First Column distillate (203) | Second Column bottoms (208) | Second Column distillate (209) |
|---|---|---|---|---|---|
| HFC-236cb (wt %) | 93.5 | 100 | 27.1 | 0.03 | 28.6 |
| PFC-C318 (wt %) | 6.5 | <1 ppm | 72.9 | 99.97 | 71.4 |
| Temperature (° C.) | 5.0 | 3.64 | −4.1 | 67.1 | 64.1 |
| Pressure (kPa) | 150 | 122 | 120 | 1000 | 1000 |

What is claimed is:
1. An azeotrope or near-azeotrope composition comprising from about 62.3 mole percent to about 71.3 mole percent PFC-C318 and from about 37.7 mole percent to about 28.7 mole percent HFC-236cb.

2. The azeotrope or near-azeotrope composition of claim 1, wherein the vapor pressure of said composition is from about 1.68 psi (11.6 kPa) to about 378 psi (2606 kPa) at a temperature of from about −50° C. to about 110° C.

3. The azeotrope or near-azeotrope composition of claim 1 wherein said composition consists essentially of from about 62.3 mole percent to about 71.3 mole percent PFC-C318 and from about 37.7 mole percent to about 28.7 mole percent HFC-236cb, wherein the vapor pressure is from about 1.68 psi (11.6 kPa) to about 378 psi (2606 kPa) at a temperature of from about −50° C. to about 110° C.

4. A process for the removal of PFC-C318 from a mixture comprising HFC-236cb and PFC-C318, said process comprising:
 a) subjecting said mixture comprising HFC-236cb and PFC-C318 to a distillation step; and
 b) removing as distillate a composition comprising an azeotrope or near-azeotrope composition comprising from about 62.3 mole percent to about 71.3 mole percent HFC-236cb and from about 37.7 mole percent to about 28.7 mole percent PFC-C318.

5. A process for the separation of PFC-C318 from a mixture comprising HFC-236cb and PFC-C318, said process comprising:
 a) subjecting said mixture to a first distillation step in which a composition enriched in either (i) PFC-C318 or (ii) HFC-236cb is removed as a first distillate composition comprising an azeotrope or near-azeotrope composition comprising from about 62.3 mole percent to about 71.3 mole percent HFC-236cb and from about 37.7 mole percent to about 28.7 mole percent PFC-C318, with a first bottoms composition being enriched in the other of said components (i) or (ii); and
 b) subjecting said first distillate composition to a second distillation step conducted at a different pressure than the first distillation step in which the component enriched as first bottoms composition in (a) is removed in a second distillate composition with a second bottoms composition enriched in the same component which was enriched in the first distillate composition.

6. The process of claim 5 wherein said first bottoms composition comprises HFC-236cb essentially free of PFC-C318.

7. The process of claim 5 wherein said second bottoms composition comprises PFC-C318 essentially free of HFC-236cb.

8. An azeotrope or near-azeotrope composition comprising from about 39.5 mole percent to about 59.5 mole percent hydrogen fluoride and from about 60.5 mole percent to about 40.5 mole percent PFC-C318.

9. The azeotrope or near-azeotrope composition of claim 8, wherein the vapor pressure of said composition is from about 1.81 psi (kPa) to about 565 psi (kPa) at a temperature of from about −50° C. to about 100° C.

10. The azeotrope or near-azeotrope composition of claim 8 wherein said composition consists essentially of from about 39.5 mole percent to about 59.5 mole percent hydrogen fluoride and from about 60.5 mole percent to about 40.5 mole percent PFC-C318, wherein the vapor pressure is from about 1.81 psi (kPa) to about 565 psi (kPa) at a temperature of from about −50° C. to about 100° C.

* * * * *